United States Patent
Nakanishi

(10) Patent No.: US 8,976,923 B2
(45) Date of Patent: Mar. 10, 2015

(54) MULTISLICE CT APPARATUS AND METHOD FOR DATA PREPROCESSING

(71) Applicants: Kabushiki Kaisha Toshiba, Minato-ku (JP); Toshiba Medical Systems Corporation, Otawara-shi (JP)

(72) Inventor: Satoru Nakanishi, Utsunomiya (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 129 days.

(21) Appl. No.: 13/900,047

(22) Filed: May 22, 2013

(65) Prior Publication Data

US 2013/0251094 A1    Sep. 26, 2013

Related U.S. Application Data

(63) Continuation of application No. PCT/JP2012/071431, filed on Aug. 24, 2012.

(30) Foreign Application Priority Data

Sep. 8, 2011  (JP) ................................ 2011-195595

(51) Int. Cl.
*A61B 6/00* (2006.01)
*G06T 11/00* (2006.01)
*A61B 6/03* (2006.01)

(52) U.S. Cl.
CPC ............. *A61B 6/5205* (2013.01); *A61B 6/5258* (2013.01); *G06T 11/005* (2013.01); *A61B 6/032* (2013.01); *A61B 6/4085* (2013.01); *A61B 6/4233* (2013.01)
USPC .................................................. 378/8; 378/4

(58) Field of Classification Search
CPC ....................................................... A61B 6/032
USPC ........................................................ 378/4–20
See application file for complete search history.

(56) References Cited

U.S. PATENT DOCUMENTS

| 7,764,763 | B2 | 7/2010 | Mori | |
|---|---|---|---|---|
| 2005/0226365 | A1* | 10/2005 | Taguchi | 378/13 |
| 2006/0280281 | A1* | 12/2006 | Flohr et al. | 378/5 |

FOREIGN PATENT DOCUMENTS

| JP | 2005-279282 | 10/2005 |
|---|---|---|
| WO | 2007-148725 | 12/2007 |

OTHER PUBLICATIONS

International Search Report mailed Nov. 6, 2012 for PCT/JP2012/071431 filed on Aug. 24, 2012 with English Translation.
International Preliminary Report on Patentability and Written Opinion issued Mar. 12, 2014 in PCT/JP2012/071431, filed Aug. 24, 2012 (submitting English translation only).

* cited by examiner

*Primary Examiner* — Hoon Song
(74) *Attorney, Agent, or Firm* — Oblon, McClelland, Maier & Neustadt, L.L.P.

(57) ABSTRACT

A multislice CT apparatus includes a setting unit, a correcting unit, a filtering unit and a reconstructing unit. The setting unit sets a weighting coefficient in such a way that data on a middle column is weighted high while data on columns on both sides of the middle column is weighted low on a middle channel in a multislice detector, and that a weight given to data on a middle column falls while a weight given to data on both side columns rises as shifting from the middle channel to an end channel. The correcting unit corrects the weighting coefficient in such a way that a weight rises as shifting from a central column to an end column. The filtering unit filters data on the basis of the corrected weighting coefficient in a column direction. The reconstructing unit reconstructs an image on the basis of the filtered data.

10 Claims, 6 Drawing Sheets

MULTISLICE CT APPARATUS AND METHOD FOR DATA PREPROCESSING

CROSS-REFERENCE TO RELATED APPLICATION

This application is a Continuation Application of No. PCT/JP2012/071431, filed on Aug. 24 2012, and the PCT application is based upon and claims the benefit of priority from Japanese Patent Application No. 2011-195595, filed on Sep. 8, 2011, the entire contents of which are incorporated herein by reference.

FIELD

The embodiment of the invention relates to a multislice CT (computed tomography) apparatus which reconstructs an image on the basis of data obtained from an object irradiated with X-rays and a method for data preprocessing.

BACKGROUND

An X-ray CT apparatus provides information on an object through an image on the basis of intensity of X-rays having passed through the object, and plays an important role in lots of medical practices such as diagnosis and treatment of disease, surgery planning, etc.

The X-ray CT apparatus includes a multislice CT (ADCT: area detector computed tomography) apparatus having a multislice detector. A helical scan of a spherical or domed object done by the use of a multislice CT apparatus causes windmill artifacts to appear on an image. The windmill artifacts are brought about by data of a plurality of columns of detecting elements incidentally just matched with one another in reconstruction. As the multislice CT apparatus does not use the same detecting element around 360 degrees all the time in the reconstruction and interpolates data between the detecting elements correspondingly to an angle, it looks as if the data on the respective columns of the detecting elements crosses over to one another. As there is a plurality of thresholds of crossing over, the windmill artifacts appear on the image.

Incidentally, a technology for reducing windmill artifacts by filtering raw data is known as art related to the invention. In this technology, a method for filtering data in a direction of columns being channel-dependent is introduced so that windmill artifacts can be dealt with in a helical scan.

The windmill artifacts are not specific to the helical scan, and conspicuously appear particularly on a cone angle end in circular orbit (CFK: circular feldkamp) reconstruction in a conventional scan. A reason for that is undersampling in the column direction similarly as in the helical scan, and requires a flying focus in the column direction so as to be solved in principle.

In the circular orbit reconstruction in the conventional scan, as described above, windmill artifacts are likely to appear not in the center of the cone angle in principle but from the central column to the end column in the multislice detector conspicuously. Thus, if the ordinary art in the helical scan is applied to the conventional scan for raw data produced close to the end column apart from the central column in the multislice detector, an effect on reduction of artifacts can be obtained on images.

If, however, the ordinary art in the helical scan is applied to the conventional scan for raw data produced close to the central column in the multislice detector, an area where no windmill artifacts appear is processed as well, resulting in that an image obtained by a detecting element in a column close to the central column in the multislice detector undergoes careless degradation of space resolution.

BRIEF DESCRIPTION OF THE DRAWINGS

In accompanying drawings.

DETAILED DESCRIPTION

Figure 1:
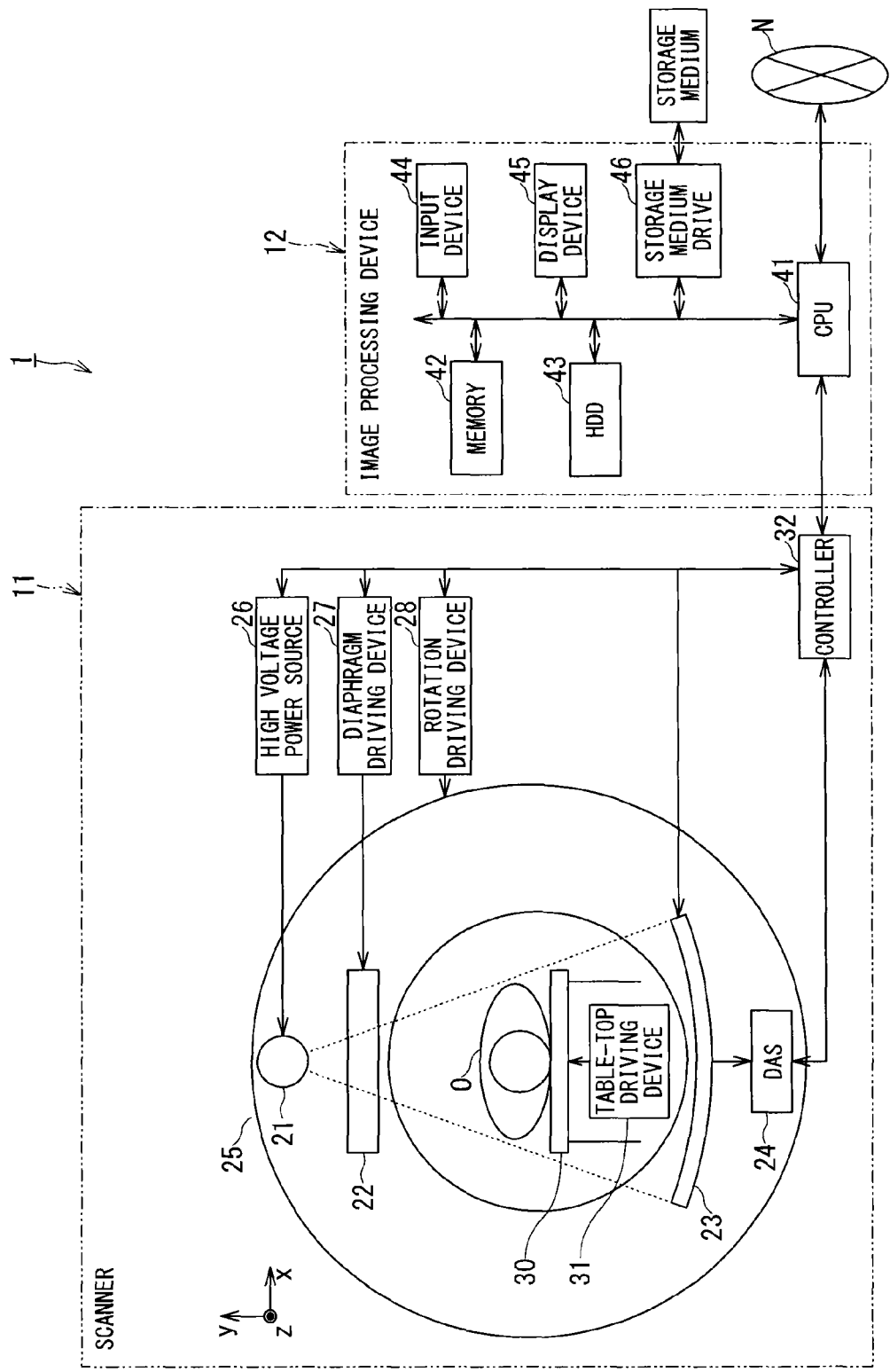
FIG. 1 is a block diagram which shows a multislice CT apparatus according to a present embodiment.

A multislice CT apparatus and a method for preprocessing data of the embodiment will be explained with reference to the drawings.

To solve the above-described problems, the present embodiments provide the multislice CT apparatus including: an X-ray source configured to produce X-rays; a multislice detector having a plurality of columns of detecting elements each being configured to detect the X-rays; a scan performing unit configured to perform a conventional scan by rotating the X-ray source and the multislice detector around an object; a weighting coefficient setting unit configured to set a weighting coefficient in such a way that data before reconstruction on a middle column is weighted high while data before reconstruction on columns on both sides of the middle column is weighted low on a middle channel in the multislice detector, and that a weight given to data before reconstruction on a middle column falls while a weight given to data before reconstruction on both side columns rises as shifting from the middle channel to an end channel; a correcting unit configured to correct the weighting coefficient in such a way that a weight rises as shifting from a central column to an end column in the multislice detector; a column direction filtering unit configured to filter data before reconstruction collected by the scan on the basis of the corrected weighting coefficient in a column direction; and an image reconstructing unit configured to reconstruct an image on the basis of the filtered data before reconstruction.

To solve the above-described problems, the present embodiments provide the method for data preprocessing including: setting a weighting coefficient in such a way that data before reconstruction on a middle column is weighted high while data before reconstruction on columns on both sides of the middle column is weighted low on a middle channel in a multislice detector, and that a weight given to data before reconstruction on a middle column falls while a weight given to data before reconstruction on both side columns rises as shifting from the middle channel to an end channel; correcting the weighting coefficient in such a way that a weight rises as shifting from a central column to an end column in the multislice detector; and filtering data before reconstruction collected by a conventional scan on the basis of the corrected weighting coefficient in a column direction.

The multislice CT apparatus according to the present embodiment includes a variety of types such as a rotation/rotation type in which an X radiation source and a multislice detector rotate around an object as an integrated unit and a stationary/rotation type in which a large number of detecting elements are arrayed in a ring form and only an X radiation source rotates around a object, and any one of the types can be applied to the present invention. Herein, the rotation/rotation type, which is in the mainstream, will be described.

A dominating mechanism for converting incident X-rays into an electric charge includes indirect conversion in which X-rays are converted into light with a fluorescent substance such as a scintillator and the light is further converted into an electric charge with a photoelectric transducer such as a photodiode, and direct conversion by means of generation of electron-hole pairs in a semiconductor by X-rays and their migration to an electrode, namely, a photoconductive phenomenon.

Additionally, what is called multi-tubular multislice CT apparatuses in which a plurality of pairs of an X radiation source and a multislice detector are mounted on a rotation ring has become commercially available in recent years, and related techniques of the multi-tubular multislice CT apparatuses have been developed. The multislice CT apparatus according to the present embodiment may be applied to any of the conventional single-tubular multislice CT apparatuses and the multi-tubular multislice CT apparatuses. Herein, a single-tubular multislice CT apparatus will be described.

FIG. 1 is a block diagram which shows a multislice CT apparatus according to the present embodiment.

FIG. 1 shows a multislice CT apparatus 1 of the present embodiment. The multislice CT apparatus 1 is broadly formed by a scanner 11 and an image processing device (console) 12. The scanner 11 of the multislice CT apparatus 1 is ordinarily installed in an examination room, and is configured to produce X-ray pass-through data regarding the part to be photographed of a patient O (object). Meanwhile, the image processing device 12 is ordinarily installed in a control room next to the examination room, and is configured to produce projection data on the basis of the pass-through data and to produce and display a reconstructed image.

The scanner 11 of the multislice CT apparatus 1 is provided with an X-ray tube (X-ray source) 21, a diaphragm 22, a multislice detector 23, a DAS (data acquisition system) 24, a rotation section 25, a high voltage power source 26, a diaphragm driving device 27, a rotation driving device 28, a table-top 30, a table-top driving device 31 and a controller 32.

The X-ray tube 21 hits a metallic target with an electron beam in accordance with a tube voltage supplied by the high voltage power source 26, and radiates the X-rays toward the multislice detector 23. The X-rays radiated by the X-ray tube 21 form fan beam X-rays or cone beam X-rays. The X-ray tube 21 is supplied with power needed for radiating X-rays as controlled by the controller 32 via the high voltage power source 26.

The diaphragm 22 adjusts a range in a slice direction (z-axis direction) to be irradiated with the X-rays radiated by the X-ray tube 21 by means of the diaphragm driving device 27. That is, the diaphragm driving device 27 adjusts an aperture of the diaphragm 22 so that the range to be irradiated with the X-rays in the slice direction can be changed.

The multislice detector 23 is a 2D array type detector having plural detecting elements in a matrix form, i.e., in both of the channel and slice directions. The multislice detector 23 detects X-rays having radiated by the X-ray tube 21 and passed through the patient O.

The DAS 24 amplifies a signal of pass-through data detected by each of the respective detecting elements of the multislice detector 23 and converts the amplified signal into a digital signal. The DAS 24 provides the image processing device 12 with output data of the DAS 24 via the controller 32 of the scanner 11.

The rotation section 25 holds the X-ray tube 21, the diaphragm 22, the multislice detector 23 and the DAS 24 as one. The rotation section 25 is configured to rotate the X-ray tube 21, the diaphragm 22, the multislice detector 23 and the DAS 24 around the patient O as one in condition that the X-ray tube 21 is put opposite the multislice detector 23. Incidentally, a direction parallel to a central axis of rotation of the rotation section 25 is defined as a z-axis direction, and a plane perpendicular to the z-axis direction is defined as including x-axis and y-axis directions.

The high voltage power source 26 supplies the X-ray tube 21 with power necessary for X-ray radiation as controlled by the controller 32.

The diaphragm driving device 27 has a mechanism to adjust the range to be irradiated with the X-rays in the slice direction on the diaphragm 22 as controlled by the controller 32.

The rotation driving device 28 has a mechanism to rotate the rotation section 25 as controlled by the controller 32 so that the rotation section 25 rotates around a cavity portion while maintaining its relative position.

The table-top 30 is a portion on which the patient O can be laid.

The table-top driving device 31 has a mechanism to move the table-top 30 up and down along the y-axis direction and inwards and outwards along the z-axis direction as controlled by the controller 32. The rotation section 25 has an aperture in its middle portion and the patient O laid on the table-top 30 is carried into the aperture.

The controller 32 is formed by a CPU (central processing unit) and a memory. The controller 32 controls the multislice detector 23, the DAS 24, the high voltage power source 26, the diaphragm driving device 27, the rotation driving device 28, the table-top driving device 31, etc., and makes them carry out a scan.

The image processing device 12 of the multislice CT apparatus 1 has a computer-based structure and can interactively communicate with a network (local area network) N. The image processing device 12 is broadly formed by basic hardware components such as a CPU 41, a memory 42, an HDD (hard disc drive) 43, an input device 44, a display device 45, etc. The CPU 41 is mutually coupled with the respective hardware components which form the image processing device 12 via a bus being a common signal transmission path. Incidentally, the image processing device 12 may sometimes have a storage medium drive 46.

The CPU 41 is a control device having a structure of an integrated circuit (LSI) in which an electronic circuit formed by a semiconductor is enclosed in a package having plural terminals. Upon being provided with instructions according to operation, etc., of the input device 45 performed by an operator such as a medical doctor, an examination engineer, etc., the CPU 41 runs a program stored in the memory 42. Otherwise, the CPU 41 loads the memory 42 with a program stored in the HDD 43, a program transferred from the network N and installed in the HDD 43 or a program read from a storage medium inserted into the storage medium drive 46 and installed in the HDD 43, and runs the program.

The memory 42 is a storage device includes a ROM (read only memory), a RAM (random access memory), etc. The memory 42 stores an IPL (initial program loader), a BIOS (basic input/output system) and data, and is used as a work memory for the CPU 41 or temporary storage of data.

The HDD 43 is a storage device having a structure in which a metallic disk not being removable that magnetic substance is applied to or laid on by vapor deposition is contained. The HDD 43 is a storage device in which a program (including an OS (operating system), etc., as well as an application program), data before reconstruction (raw data and projection data), or data after reconstruction (image data) is stored. Further, it is practical to make the OS provide a GUI (graphical user interface) in which graphics are used a lot for presenting information to the operator and basic operations can be done by means of the input device 44.

The input device 44 is a pointing device that the operator can operate, and an input signal according to an operation is sent to the CPU 41.

The display device 45 includes an image composing circuit, a VRAM (video random access memory), a display monitor, etc., which are not shown. The image composing circuit combines image data with text data of various parameters so as to produce composed data. The VRAM unfolds the composed data as display image data to be displayed on the display monitor. The display monitor is formed by an LCD monitor, a CRT (cathode ray tube), etc., and displays the display image data as displayed images in turn.

The storage medium drive 46 is configured to be loaded with a removable storage medium, reads data (including a program) stored in the storage medium so as to output the read data onto the bus, and writes data provided via the bus into the storage medium. So called package software can be provided as being stored in such a storage medium.

The image processing device 12 performs a logarithmic transformation process and a correction process for correcting sensitivity (preprocess), etc., on the raw data provided by the DAS 24 of the scanner 11 so as to produce projection data and stores the projection data in the storage devices such as the HDD 43. Further, the image processing device 12 performs a process for removing scattered radiation on the preprocessed projection data. The image processing device 12 removes scattered radiation on the basis of a value of projection data within an X-ray exposure range and performs scattered radiation correction by subtracting scattered radiation estimated according to a value of projection data of a target of the scattered radiation correction or of projection data next to that from the projection data of the target. The image processing device 12 performs segment reconstruction on the basis of the corrected projection data so as to produce image data and to store the image data in the storage devices such as the HDD 43.

Figure 2:
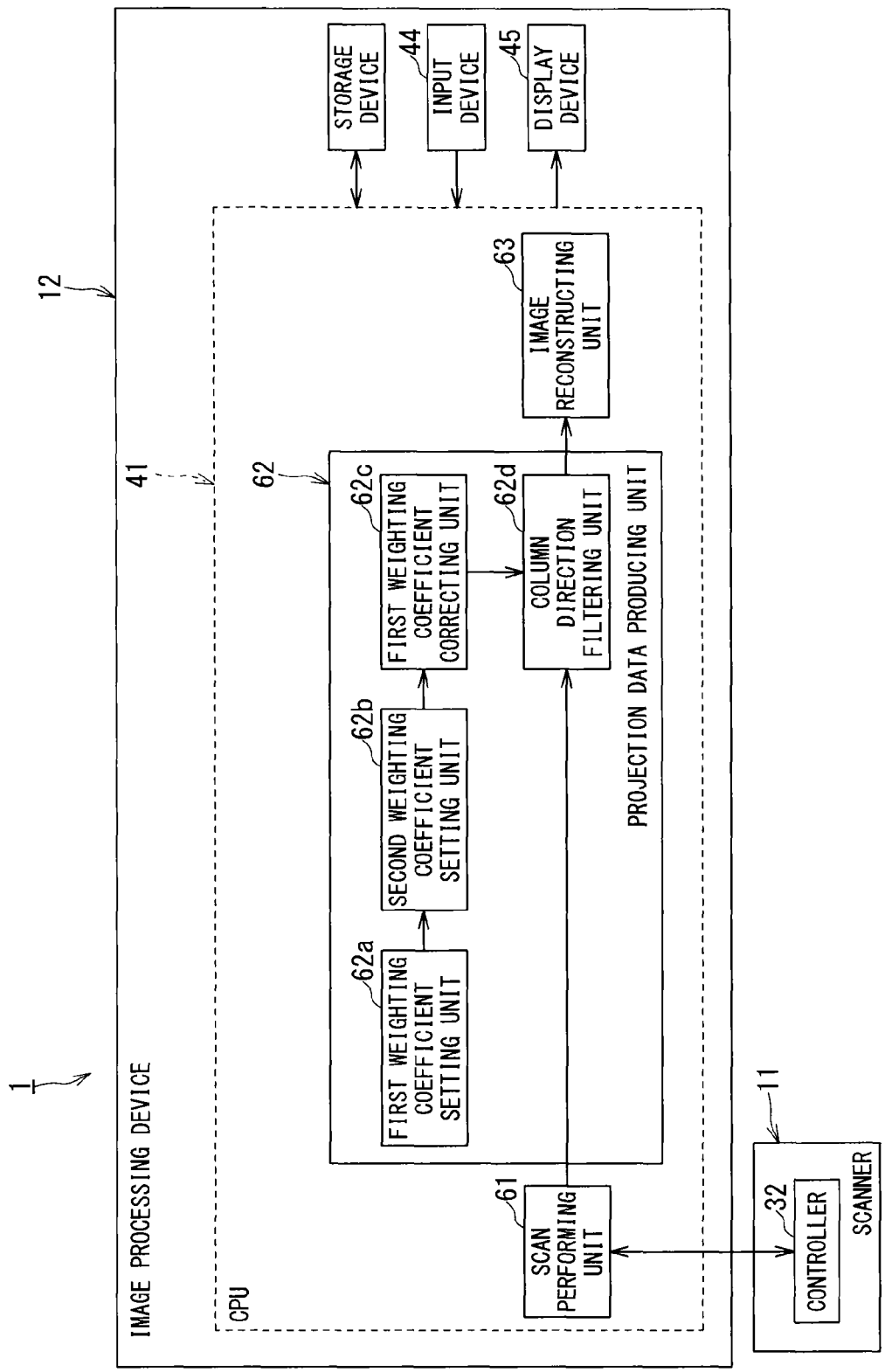
FIG. 2 is a block diagram which shows a function of the multislice CT apparatus according to the present embodiment.

FIG. 2 is a block diagram which shows a function of the multislice CT apparatus 1 according to the present embodiment.

The CPU 41 (or the controller 32) shown in FIG. 1 runs a program so that the multislice CT apparatus 1 works as a scan performing unit 61, a projection data producing unit (preprocessor) 62 and an image reconstructing unit 63. Incidentally, although it is supposed that the respective portions 61-63 forming the multislice CT apparatus 1 each function as the CPU 41 runs a program, the configuration of the multislice CT apparatus 1 is not limited to such a case. The multislice CT apparatus 1 may be equipped with all or part of the respective portions 61-63 forming the multislice CT apparatus 1 in hardware forms.

The scan performing unit 61 has a function to control the controller 32 of the scanner 11 so as to perform a conventional scan (non-helical scan, volume scan) for an area including the part to be photographed of the patient O laid on the table-top 30 according to scan conditions.

The projection data producing unit 62 has a function to preprocess raw data collected by the scan performed by the scan performing unit 61 corresponding to a plurality of columns of detecting elements in the multislice detector 23 so as to produce projection data corresponding to the plural columns of detecting elements. The projection data producing unit 62 has a first weighting coefficient setting unit 62a, a second weighting coefficient setting unit 62b, a first weighting coefficient correcting unit 62c and a column direction filtering unit 62d.

The first weighting coefficient setting unit 62a has a function to set a first weighting coefficient in such a way that raw data on a middle column is weighted high while raw data on columns on both sides of the middle column is weighted low on a middle channel in the multislice detector 23, and that a weight given to raw data on a middle column rises while a weight given to raw data on both side columns falls as shifting from the middle channel to an end channel.

Suppose, e.g., that raw data on three columns close to one another in the multislice detector 23 is weighted and added in the column direction. The first weighting coefficient changes depending upon a radius from a rotation center of a pixel corresponding to a detecting element (channel). That is, the weight changes depending upon the channel direction as well as upon a view and a column. Sharpness is set high on the rotation center according to a filter characteristic, i.e., data is highly dominated by the middle column, and sharpness is set lower farther apart from the rotation center. If a combination of weights is written as (weight for raw data on one side column, weight for raw data on middle column, weight for raw data on another side column), the rotation center (central channel) is given (0, 1, 0), and a farthest end channel is given (0.3, 0.4, 0.3). The weight gradually changes between them from (0, 1, 0) to (0.3, 0.4, 0.3).

The second weighting coefficient setting unit 62b has a function to set a second weighting coefficient which rises as shifting from a central column to an end column in the multislice detector 23.

Figure 3A:
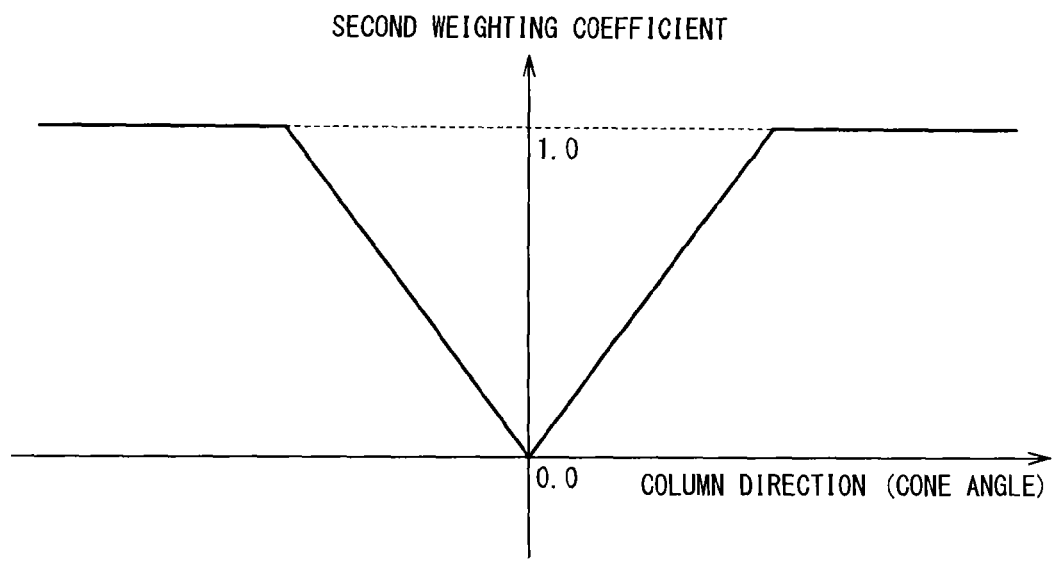
FIGS. 3A and 3B are diagrams which each shows example of the second weighting coefficient.
Figure 3B:
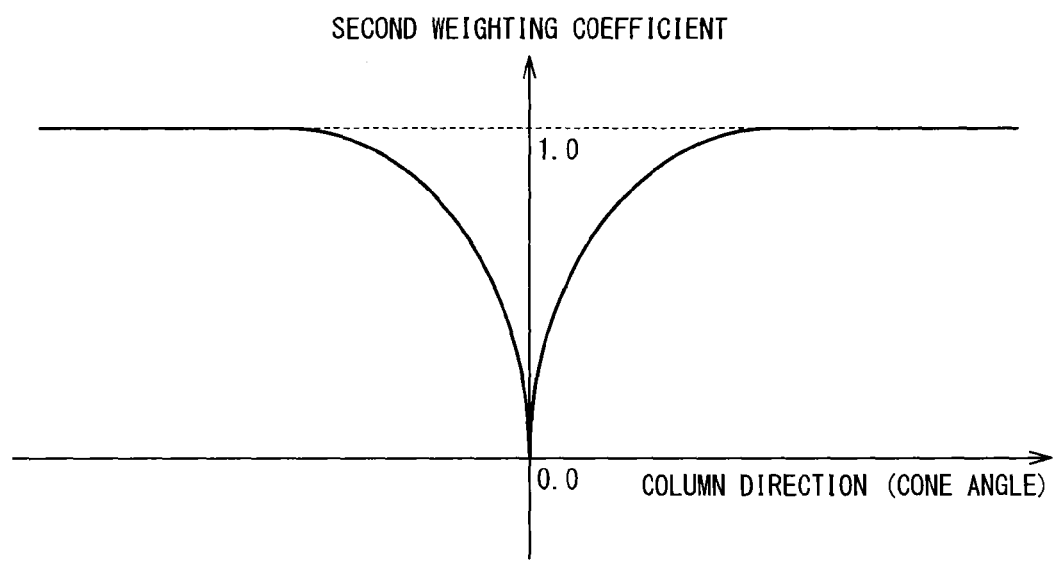

FIGS. 3A and 3B are diagrams which each shows example of the second weighting coefficient.

As shown in FIGS. 3A and 3B, the second weighting coefficient setting unit 62b sets the second weighting coefficient for weighting and adding the first weighting coefficient so that the first weighting coefficient rises as shifting from the central column to the end column. Thus, filtering strength by the first weighting coefficient is zero on the middle column (center of cone angle) in the multislice detector 23, and the farther apart from the middle column, the more the filtering strength by the first weighting coefficient can be obtained.

The first weighting coefficient correcting unit 62c has a function to correct the first weighting coefficient set by the first weighting coefficient setting unit 62a with the second weighting coefficient set by the second weighting coefficient setting unit 62b so as to produce a first weighting coefficient after the correction. The first weighting coefficient set by the first weighting coefficient setting unit 62a and the second weighting coefficient set by the second weighting coefficient setting unit 62b may be stored in the storage device such as the HDD 43 in advance. In that case, the first weighting coefficient correcting unit 62c reads the first weighting coefficient and the second weighting coefficient from the storage device and produces the first weighting coefficient after the correction.

Figure 4:
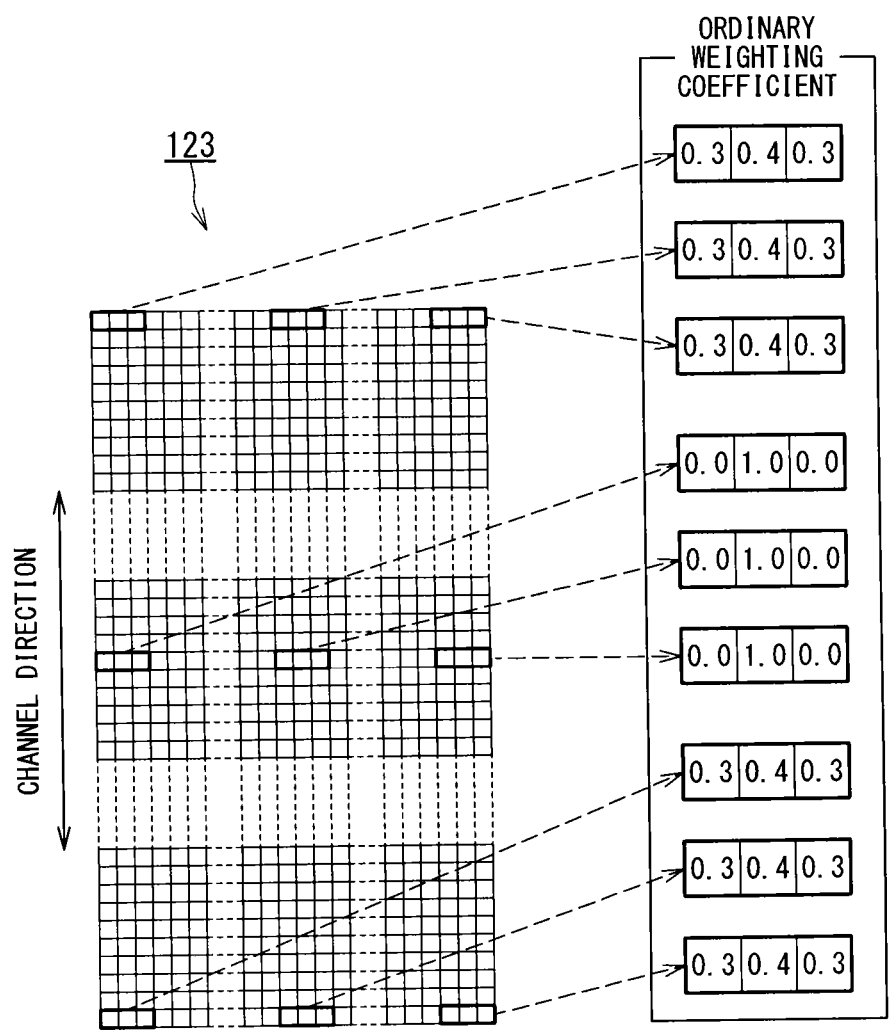
FIG. 4 is a diagram which shows an ordinary weighting coefficient.

FIG. 4 is a diagram which shows an ordinary weighting coefficient.

FIG. 4 shows an ordinary multislice detector 123 and a weighting coefficient set to each of locations in the multislice detector 123. The ordinary weighting coefficient corresponds to the first weighting coefficient of the embodiment. On a middle channel of the ordinary multislice detector 123, raw data on a middle column is weighted high, while raw data on columns on both sides of the middle column is weighted low. Besides, a weight given to raw data on a middle column falls while a weight given to raw data on both side columns rises as shifting from the middle channel to an end channel.

Figure 5:
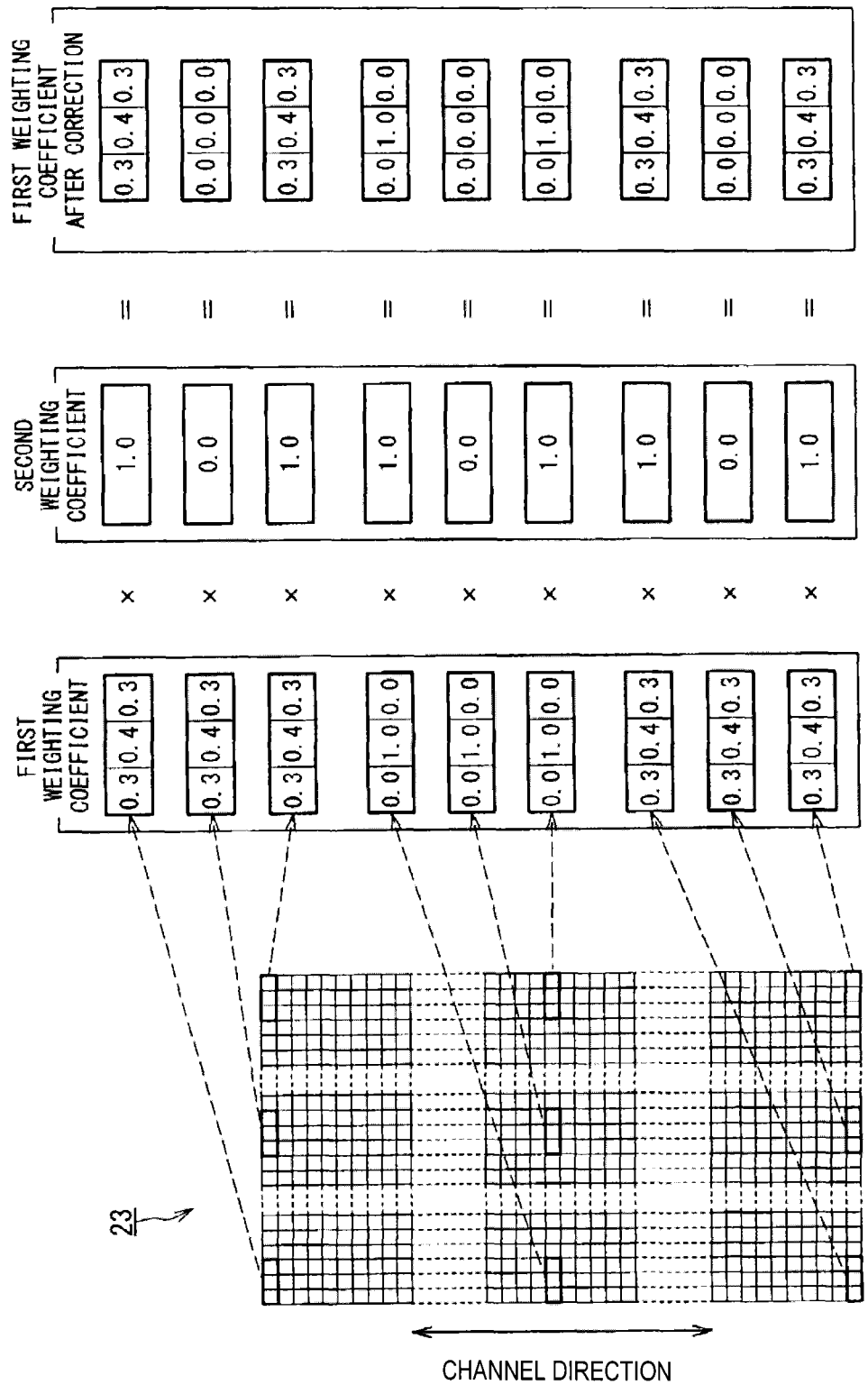
FIG. 5 is a diagram which shows a weighting coefficient (first weighting coefficient after correction) according to the present embodiment.

FIG. 5 is a diagram which shows a weighting coefficient (first weighting coefficient after correction) according to the present embodiment.

FIG. 5 shows the multislice detector 23 of the embodiment and a weighting coefficient after correction set to each of locations in the multislice detector 23.

As shown in FIG. 5, the ordinary weighting coefficient (first weighting coefficient) shown in FIG. 4 is weighted with the second weighting coefficient shown in FIGS. 3A and 3B so that the first weighting coefficient after the correction is produced. The first weighting coefficient (0.3, 0.4, 0.3) given to raw data on an end channel and an end column, e.g., multiplied by the second weighting coefficient 1.0 is the first weighting coefficient after the correction (0.3, 0.4, 0.3). Further, the first weighting coefficient (0.3, 0.4, 0.3) given to raw data on the end channel and the middle column multiplied by the second weighting coefficient 0.0 is the first weighting coefficient after the correction (0.0, 0.0, 0.0).

Further, the first weighting coefficient (0.0, 1.0, 0.0) given to raw data on the middle channel and the end column in the multislice detector 23 multiplied by the second weighting coefficient 1.0 is a first weighting coefficient after the correction (0.0, 1.0, 0.0). Further, the first weighting coefficient (0.0, 1.0, 0.0) given to raw data on the middle channel and the middle column in the multislice detector 23 multiplied by the second weighting coefficient 0.0 is a first weighting coefficient after the correction (0.0, 0.0, 0.0).

The column direction filtering unit 62d shown in FIG. 2 has a function to filter raw data collected by the scan performing unit 61 corresponding to the plural columns of detecting elements in the column direction on the basis of the first weighting coefficient after the correction produced by the first weighting coefficient correcting unit 62c. If three columns next to one another are made targets, the first weighting coefficient correcting unit 62c weights and adds raw data of three columns of the same channel number.

The image reconstructing unit 63 has a function to reconstruct a plurality of slice images on the basis of the projection data produced by the projection data producing unit 62. The plural slice images produced by the image reconstructing unit 63 are displayed on the display device 45 or stored in the storage device such as the HDD 43.

Figure 6:
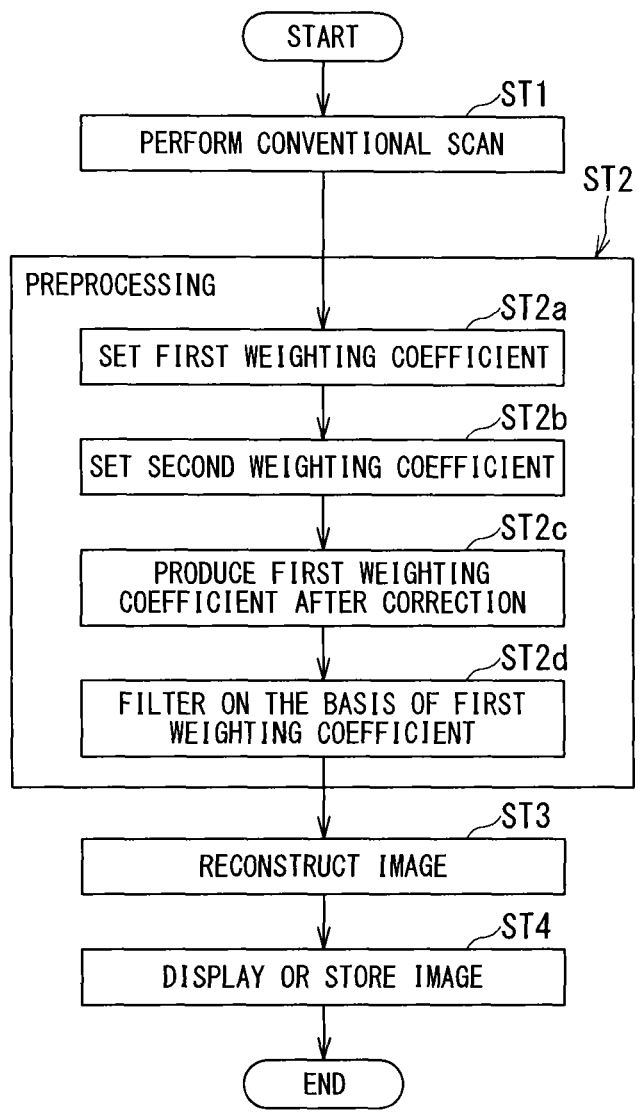
FIG. 6 is a diagram which shows a flowchart illustrating an operation of the multislice CT apparatus according to the present embodiment.

Then, an operation of the multislice CT apparatus 1 will be explained by the use of a flowchart shown in FIG. 6.

The multislice CT apparatus 1 controls the controller 32 of the scanner 11 at first so as to perform a conventional scan (non-helical scan, volume scan) for an area including the part to be photographed of the patient O laid on the table-top 30 according to scan conditions (step ST1). Then, the multislice CT apparatus 1 preprocesses raw data collected by the scan performed at the step ST1 corresponding to the plural columns of detecting elements in the multislice detector 23 so as to produce projection data corresponding to the plural columns of detecting elements (step ST2).

The multislice CT apparatus 1 sets a first weighting coefficient at the step ST2 in such a way that raw data on a middle column is weighted high while raw data on columns on both sides of the middle column is weighted low on a middle channel in the multislice detector 23, and that a weight given to raw data on a middle column rises while a weight given to raw data on both side columns falls as shifting from the middle channel to an end channel (step ST2a).

Then, the multislice CT apparatus 1 sets a second weighting coefficient which rises as shifting from the central column to the end column in the multislice detector 23 as shown in FIGS. 3A and 3B (step ST2b). Owing to the step ST2b, filtering strength by the first weighting coefficient is zero on the middle column (center of cone angle) in the multislice detector 23, and the farther apart from the middle column, the more the filtering strength by the first weighting coefficient can be obtained.

Then, the multislice CT apparatus 1 corrects the first weighting coefficient set at the step ST2a with the second weighting coefficient set at the step ST2b so as to produce a first weighting coefficient after the correction (step ST2c). An example of the first weighting coefficient after the correction has been explained by the use of FIG. 5. Then, the multislice CT apparatus 1 filters raw data collected at the step ST1 corresponding to the plural columns of detecting elements in the column direction on the basis of the first weighting coefficient after the correction produced at the step ST2c (step ST2d).

Then, the multislice CT apparatus 1 reconstructs an image on the basis of the projection data produced at the step ST2 (step ST3). The image produced at the step ST3 is displayed on the display device 45 or stored in the storage device such as the HDD 43 (step ST4).

According to the multislice CT apparatus 1 and the method for preprocessing data of the present invention, raw data is filtered in the column direction by the use of a first weighting coefficient that a weighting coefficient in the helical scan is corrected into, so that windmill artifacts can be suppressed around an end column apart from a central column in the multislice detector 23 and that careless degradation of space resolution cab be prevented from occurring around the central column.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A multislice CT apparatus comprising:
an X-ray source configured to produce X-rays;
a multislice detector having a plurality of columns of detecting elements each being configured to detect the X-rays;
a scan performing unit configured to perform a conventional scan by rotating the X-ray source and the multislice detector around an object;
a weighting coefficient setting unit configured to set a weighting coefficient in such a way that data before reconstruction on a middle column is weighted high while data before reconstruction on columns on both sides of the middle column is weighted low on a middle channel in the multislice detector, and that a weight given to data before reconstruction on a middle column falls while a weight given to data before reconstruction on both side columns rises as shifting from the middle channel to an end channel;

a correcting unit configured to correct the weighting coefficient in such a way that a weight rises as shifting from a central column to an end column in the multislice detector;

a column direction filtering unit configured to filter data before reconstruction collected by the scan on the basis of the corrected weighting coefficient in a column direction; and an image reconstructing unit configured to reconstruct an image on the basis of the filtered data before reconstruction.

2. The multislice CT apparatus according to claim 1, wherein:

the weighting coefficient setting unit sets the weighting coefficient as a first weighting coefficient; and the correcting unit sets a second weighting coefficient in such a way that the weight rises as shifting from the central column to the end column in the multislice detector, the correcting unit being configured to set a third weighting coefficient as the corrected weighting coefficient on the basis of the first weighting coefficient and the second weighting coefficient.

3. The multislice CT apparatus according to claim 2, wherein the correcting unit sets the weight rising linearly or in a curvilinear manner as shifting from the central column to the end column in the multislice detector.

4. The multislice CT apparatus according to claim 1, wherein:

the column direction filtering unit filters raw data being the data before reconstruction on the basis of the corrected weighting coefficient in the column direction so as to produce projection data; and the image reconstructing unit reconstructs an image on the basis of the projection data.

5. The multislice CT apparatus according to claim 1, wherein the correcting unit corrects the weighting coefficient in such a way that the weight is zero on the middle column in the multislice detector.

6. A method for preprocessing data comprising:

setting a weighting coefficient in such a way that data before reconstruction on a middle column is weighted high while data before reconstruction on columns on both sides of the middle column is weighted low on a middle channel in a multislice detector, and that a weight given to data before reconstruction on a middle column falls while a weight given to data before reconstruction on both side columns rises as shifting from the middle channel to an end channel;

correcting the weighting coefficient in such a way that a weight rises as shifting from a central column to an end column in the multislice detector; and filtering data before reconstruction collected by a conventional scan on the basis of the corrected weighting coefficient in a column direction.

7. The method for preprocessing data according to claim 6, wherein:

the weighting coefficient is set as a first weighting coefficient at a step for setting the weighting coefficient; and a second weighting coefficient is set in such a way that the weight rises as shifting from the central column to the end column in the multislice detector, and a third weighting coefficient is set as the corrected weighting coefficient on the basis of the first weighting coefficient and the second weighting coefficient at a step for correcting the weighting coefficient.

8. The method for preprocessing data according to claim 7, wherein the second weighting coefficient is set in such a way that the weight rises linearly or in a curvilinear manner as shifting from the central column to the end column in the multislice detector at a step for correcting the weighting coefficient.

9. The method for preprocessing data according to claim 6, wherein raw data being the data before reconstruction is filtered on the basis of the corrected weighting coefficient in the column direction so that projection data is produced at a step for filtering in the column direction.

10. The method for preprocessing data according to claim 6, wherein the weighting coefficient is corrected in such a way that the weight is zero on the middle column in the multislice detector at a step for correcting the weighting coefficient.

* * * * *